(12) United States Patent
Williams et al.

(10) Patent No.: US 6,872,220 B2
(45) Date of Patent: Mar. 29, 2005

(54) INFANT PHOTOTHERAPY POSITIONING SYSTEM

(75) Inventors: Jeffrey B. Williams, Ravenna, OH (US); James T. Burke, Brooklyn, OH (US); Bryan M. Merritt, East Cleveland, OH (US)

(73) Assignee: Lumitex, Inc., Strongsville, OH (US)

( * ) Notice: Subject to any disclaimer, the term of this patent is extended or adjusted under 35 U.S.C. 154(b) by 0 days.

(21) Appl. No.: 10/345,780

(22) Filed: Jan. 16, 2003

(65) Prior Publication Data

US 2004/0143307 A1 Jul. 22, 2004

(51) Int. Cl.[7] ............................................. A61N 5/06
(52) U.S. Cl. ............................................. 607/88; 128/872
(58) Field of Search ..................... 607/88–89, 872; 128/872

(56) References Cited

U.S. PATENT DOCUMENTS

| | | | |
|---|---|---|---|
| 4,761,047 A | * | 8/1988 | Mori ........................... 607/88 |
| 4,907,132 A | | 3/1990 | Parker |
| 5,005,108 A | | 4/1991 | Pristash et al. |
| 5,792,214 A | * | 8/1998 | Larsson et al. ............... 607/88 |
| 6,030,089 A | | 2/2000 | Parker et al. |
| 6,045,575 A | * | 4/2000 | Rosen et al. .................. 607/88 |
| 6,290,713 B1 | | 9/2001 | Russell |
| 6,596,016 B1 | * | 7/2003 | Vreman et al. ............... 607/88 |
| 6,811,563 B2 | | 11/2004 | Savage et al. ................ 607/88 |
| 2004/0039428 A1 | * | 2/2004 | Williams et al. .............. 607/88 |

FOREIGN PATENT DOCUMENTS

WO     WO 00/50807     8/2000

OTHER PUBLICATIONS

Two pages from Children's Medical Ventures Product Catalog 2000–2001, vol. 10, Issue 900.

* cited by examiner

Primary Examiner—Lee S Cohen
Assistant Examiner—Henry M Johnson, III
(74) Attorney, Agent, or Firm—Renner, Otto, Boisselle & Sklar, LLP

(57) ABSTRACT

A phototherapy system includes a flexible pad for positioning an infant during phototherapy treatment and one or more light emitters for directing light through portions of the pad for exposing the infant's skin to the light during phototherapy treatment. The pad may include pockets and/or other attachment means for attaching one or more light emitters to the pad bottom and/or to one or more padded side walls.

30 Claims, 6 Drawing Sheets

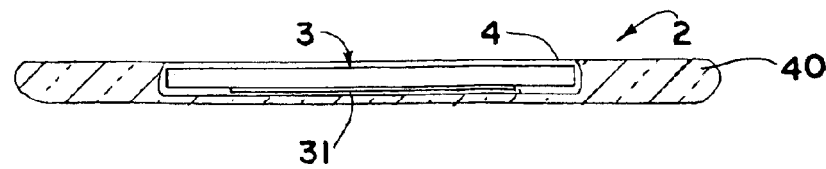
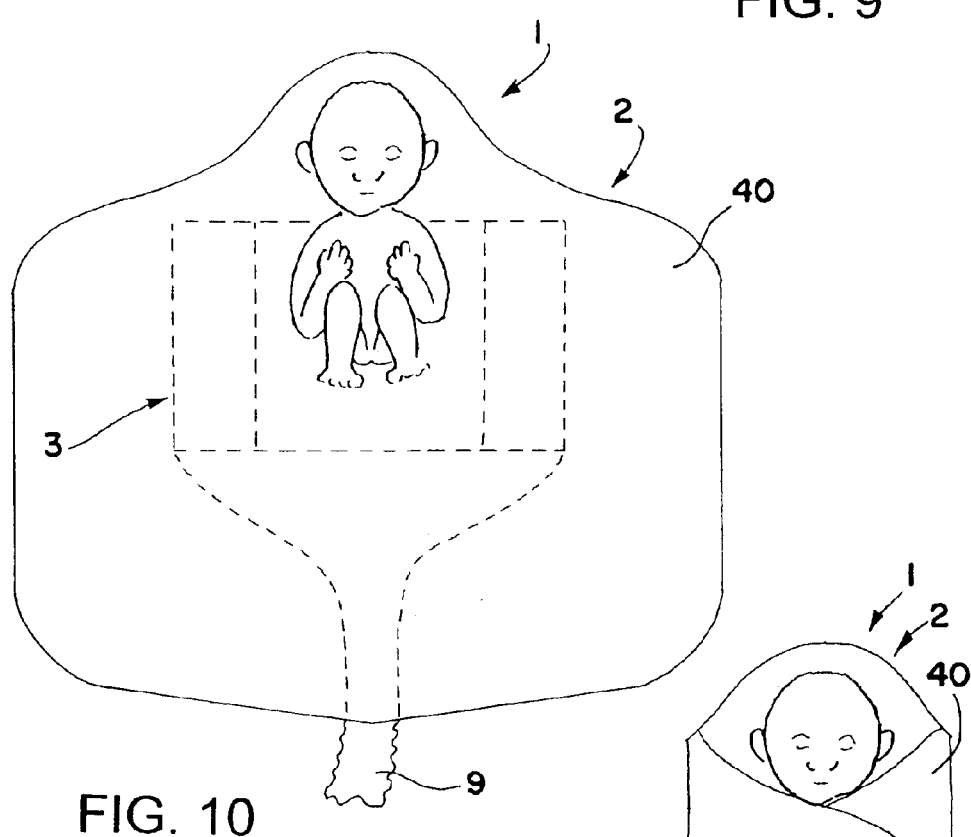
FIG. 9
FIG. 10
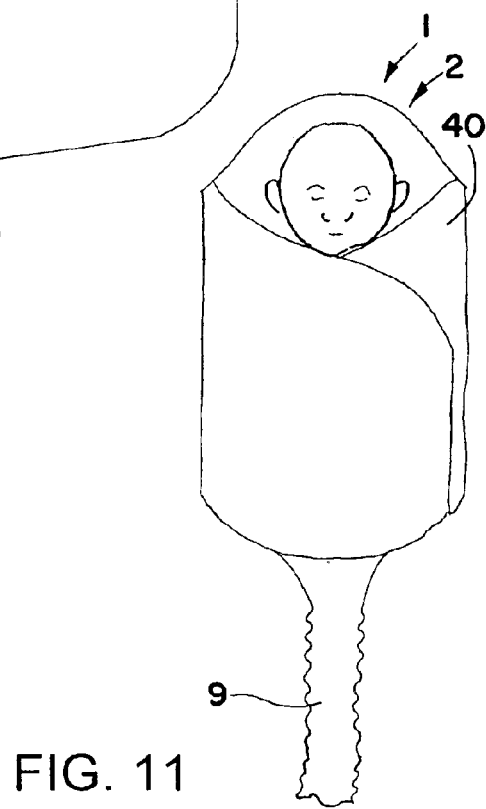
FIG. 11

INFANT PHOTOTHERAPY POSITIONING SYSTEM

FIELD OF THE INVENTION

This invention relates to a phototherapy positioning system for use in positioning and restraining an infant during phototherapy treatment and the like.

BACKGROUND OF THE INVENTION

Phototherapy has long been used to treat newborn infants for various maladies including jaundice. Jaundice is caused by a build up of bilirubin in the blood of infants. Exposing the infant's skin to certain types of light will quickly reduce the bilirubin to a safe level.

One type of phototherapy system that is commonly used in phototherapy treatment of jaundice in newborn infants is a fiber optic light pad. Also it is known to use a wrap-around vest to securely hold the fiber optic light pad in place against the infant's skin. However, there is a need for a phototherapy system that is capable of positioning the infant in a fetal type position or as dictated by the care giver to minimize stress on the infant during phototherapy treatment.

SUMMARY OF THE INVENTION

The phototherapy positioning system of the present invention allows the care giver to position the infant in any desired position during phototherapy treatment including a fetal type position to minimize stress on the infant during phototherapy treatment.

In accordance with one aspect of the invention, the phototherapy positioning system includes a flexible cloth-like pad for positioning the infant and a phototherapy light emitter attached to the pad for directing light through at least portions of the pad for exposing the infant's skin to the light during phototherapy treatment.

In accordance with another aspect of the invention, the pad may include a bottom and/or sides to which the light emitter may be attached for directing light toward the infant during phototherapy treatment.

In accordance with another aspect of the invention, the light emitter may comprise an optic light guide made of one or more layers of flexible optical fibers or molded as one piece.

In accordance with another aspect of the invention, the sides of the flexible optical fiber light emitter may be folded over to permit the light emitter to be used with different width pads.

In accordance with another aspect of the invention, the light emitter may comprise an array of lights.

In accordance with another aspect of the invention, the pad may include one or more pockets for receiving one or more light emitters.

In accordance with another aspect of the invention, the pad may include one or more fastening means such as snaps, buckles, Velcro, clips, adhesive strips and/or ties for use in attaching one or more light emitters to the pad.

In accordance with another aspect of the invention, the pad may be in the form of a blanket that is foldable around the infant and includes means for attaching a phototherapy light emitter to the blanket for directing light through at least portions of the blanket to expose the infant's skin to the light during phototherapy treatment.

In accordance with another aspect of the invention, the phototherapy positioning system may include one or more ties, snaps, buckles and/or Velcro and the like for use in positioning and restraining the infant, including the infant's arms, shoulders, hips and/or legs, on the pad during phototherapy treatment.

These and other objects, advantages, features and aspects of the invention will become apparent as the following description proceeds.

To the accomplishment of the foregoing and related ends, the invention, then, comprises the features hereinafter more fully described and particularly pointed out in the claims, the following description and the annexed drawings setting forth in detail certain illustrative embodiments of the invention, these being indicative, however, of but several of the various ways in which the principles of the invention may be employed.

BRIEF DESCRIPTION OF THE DRAWINGS

In the annexed drawings:

FIG. 9 is a schematic transverse section through the phototherapy positioning system of FIG. 8.

FIG. 10 is a schematic top plan view of the phototherapy positioning system of FIG. 8 showing an infant placed on the blanket.

FIG. 11 is a schematic top plan view similar to FIG. 10 but showing the blanket wrapped around the infant.

DETAILED DESCRIPTION OF THE INVENTION

Figure 1:
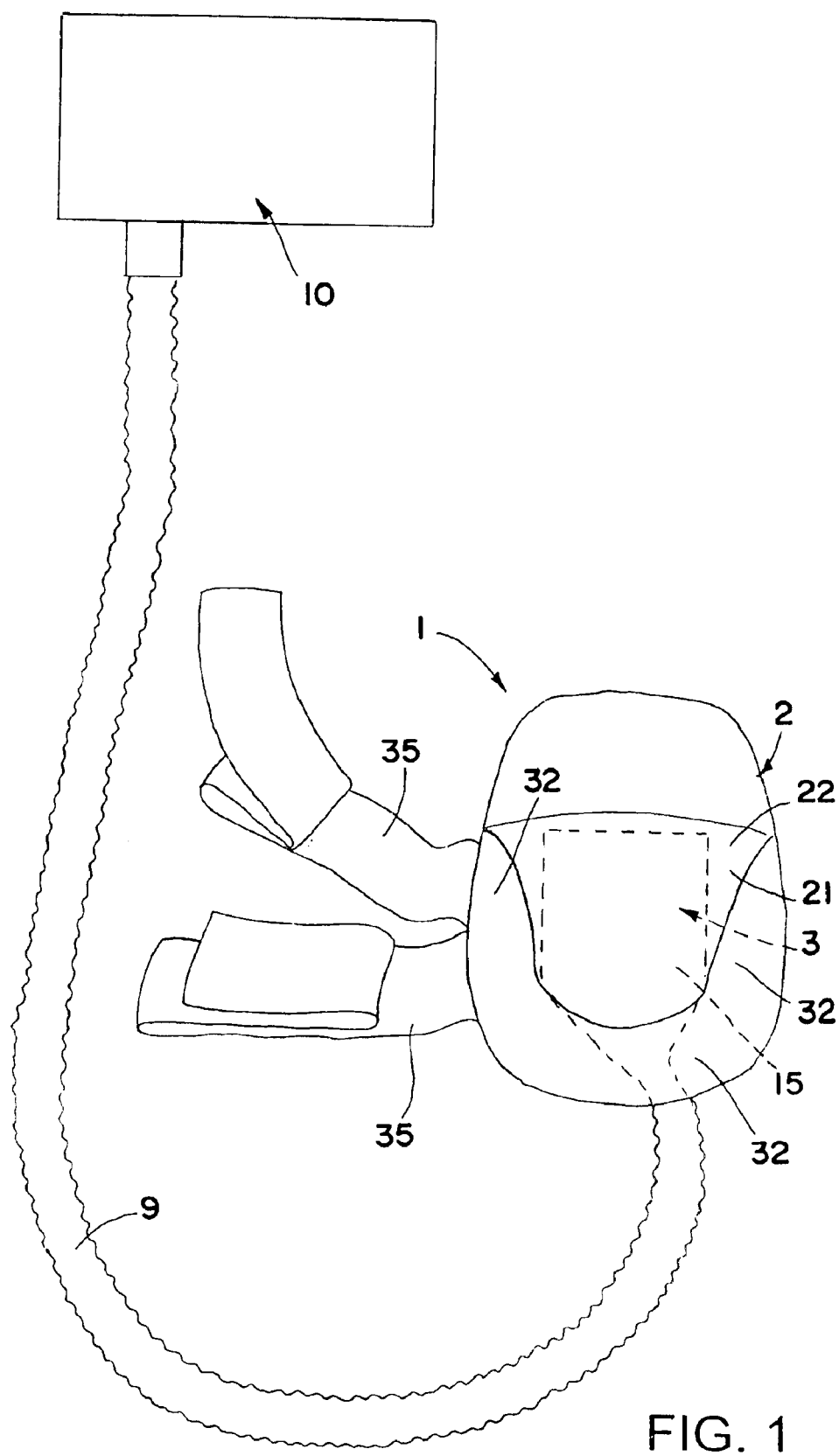
FIG. 1 is a schematic top plan view of one form of phototherapy positioning system of the present invention for use in positioning an infant during phototherapy treatment.
Figure 2A:
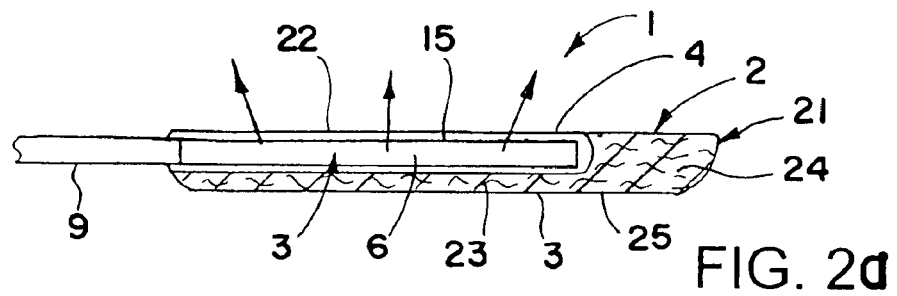
FIGS. 2a–2c are schematic fragmentary longitudinal sections through the bottom of the pad of the phototherapy positioning system of FIG. 1 showing different ways of attaching a phototherapy light emitter to the pad.
Figure 2B:
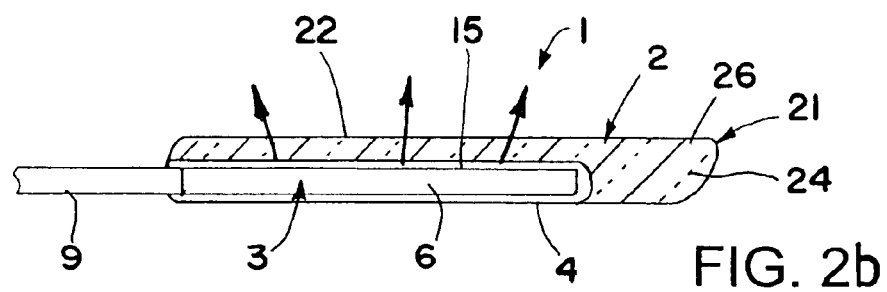
Figure 2C:
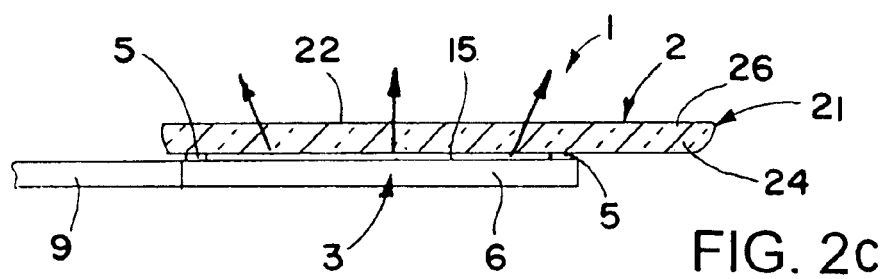

Referring now in detail to the drawings, and initially to FIGS. 1 and 2, there is shown one form of phototherapy positioning system 1 according to this invention including a flexible cloth-like pad 2 for use in positioning an infant during phototherapy treatment. Attached to pad 2 are one or more phototherapy light emitters 3 for directing right toward the infant for exposing the Infant's skin to the light during phototherapy treatment as described hereafter. FIGS. 2a and 2b show light emitter 3 received within a pocket 4 in pad 2, whereas FIG. 2c shows light emitter 3 attached to the pad using suitable attachment means 5 which may comprise for example one or more snaps, buckles, Velcro fasteners, clips, adhesive strips and/or ties and the like.

Figure 3A:
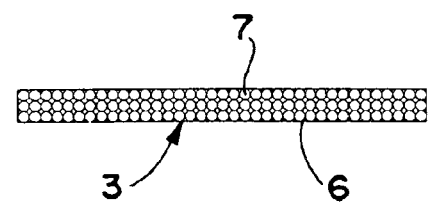
FIGS. 3a–3c are schematic transverse sections showing different types of phototherapy light emitters that may be used with the phototherapy positioning system of the present invention.
Figure 3B:
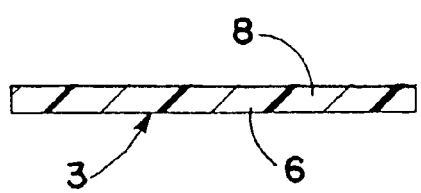

Light emitter 3 may be an optic light guide 6 which may either be comprised of one or more layers of flexible optical fibers 7 as shown in FIG. 3a or a flexible or rigid solid molded light guide 8 as shown in FIG. 3b. Light may be transmitted to the optic light guide 6 of FIGS. 3a and 3b through a flexible light distributor 9 via internal reflection from a remote light source 10 (see FIG. 1). The light emitting surface 15 of light guide 6 is larger than the cross sectional area of light distributor 9 to reduce energy density by spreading the light over a larger surface area at the light emitting surface.

Any suitable light source 10 may be used for supplying light to light guide 6, including for example incandescent, halogen, xenon, metal-halide, light emitting diodes (LED) (including organic light emitting diodes (OLED) and polymer light emitting diodes (PLED)), and fluorescent.

Figure 3C:
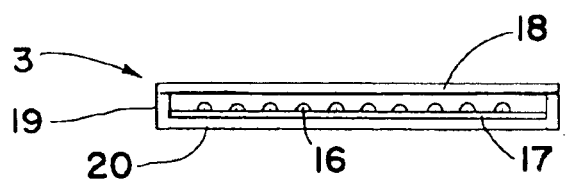

Alternatively, light emitter 3 may comprise an array of LEDs or other light sources 16 mounted on a printed circuit board 17 as schematically shown in FIG. 3c for directing light through a transparent member 18 which may be a diffuser or lens. Transparent member 18 is maintained in spaced apart relation from printed circuit board 17 and light sources 16 mounted thereon by a plurality of upstanding supports 19 on a base 20 for the circuit board.

Pad 2 includes a pad bottom 21 comprised of two or more layers of a woven fabric, or if disposable, two or more layers of a spun woven paper-like material. A top layer 22 of pad bottom 21 that is next to the infant's skin should be made out of a soft fabric-like material that is relatively light transmissive. The top fabric layer 22 can be relatively thin and/or loosely woven or the fabric fibers themselves can be relatively transparent or translucent to permit light to pass therethrough. If the light emitter 3 is a fiber optic light guide 6 that is relatively flexible, the pad bottom may include a pocket 4 immediately below the top layer 22 of fabric for receipt of the light emitter as schematically shown in FIG. 2a. A second chamber or pocket 23 may be provided below pocket 4 for receipt of a soft fill material 24 made for example of cotton batting or polyester. Also the bottom fabric layer 25 of pad 2 may be quilted to provide added softness. Further, the fill material may act as insulation to help the infant retain warmth.

If light emitter 3 is relatively rigid, the fill material or padding layer 24 should be located in a pocket or chamber 26 above the light emitter as schematically shown in FIGS. 2b and 2c. In that event, the fill material 24 should be made of a relatively transparent or translucent medium such as a clear gel. A second pocket 4 may be provided in the pad bottom below the fill material pocket 26 for receipt of light emitter 3 as shown in FIG. 2b. Alternatively light emitter 3 may be attached to the bottom of the pad using suitable fasteners 5 as previously described and schematically shown in FIG. 2c. Moreover, light emitter 3 may be removable from pocket 4 or from the pad bottom to permit the light emitter to be reused with other pads or may be integrated into the pad, making the light emitter disposable along with the pad as desired.

Figure 4A:
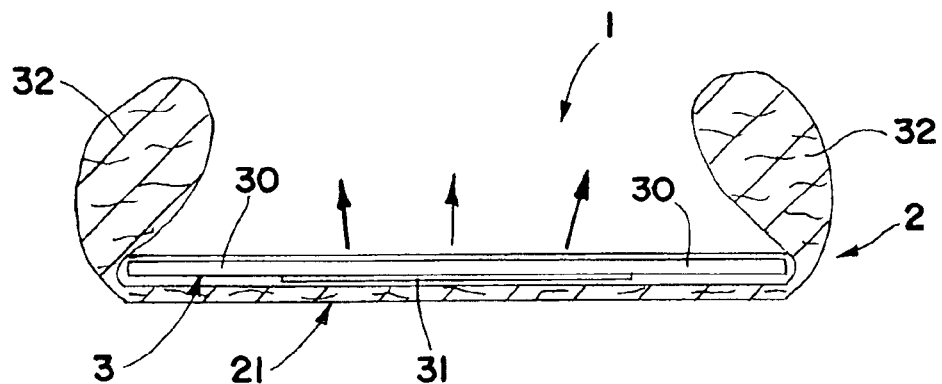
FIGS. 4a and 4b are schematic transverse sections through different width phototherapy positioning systems of the present invention showing how one size light emitter may be used with different width pads.
Figure 4B:
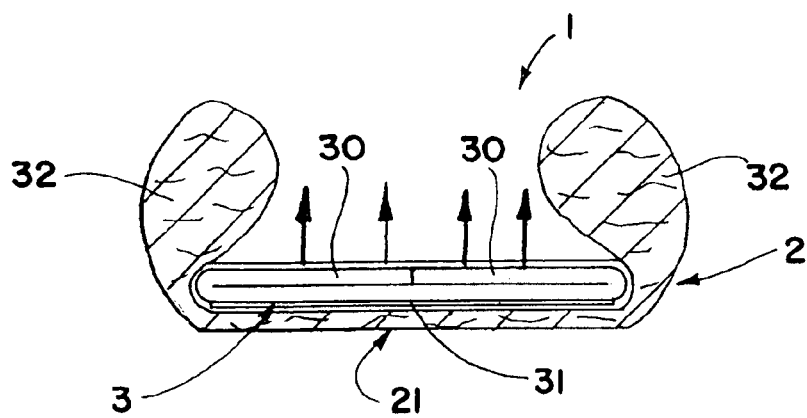

If light emitter 3 is made of one or more layers of flexible optical fibers 7, a relatively wide light emitter may be used with different width pads by leaving the light emitter substantially unfolded for use with larger width pads as schematically shown in FIG. 4a and by folding the sides 30 of the light emitter over the top surface of the light emitter to fit smaller width pads 2 as schematically shown in FIG. 4b. Also light emitter 3 may be provided with a back reflector 31. However, if the sides 30 are folded over for use with different width pads, the back reflector should terminate short of the folded sides 30 so the back reflector does not interfere with the light emitted by the light emitter along the sides when the sides are folded over as schematically shown in FIG. 4b.

Figure 5:
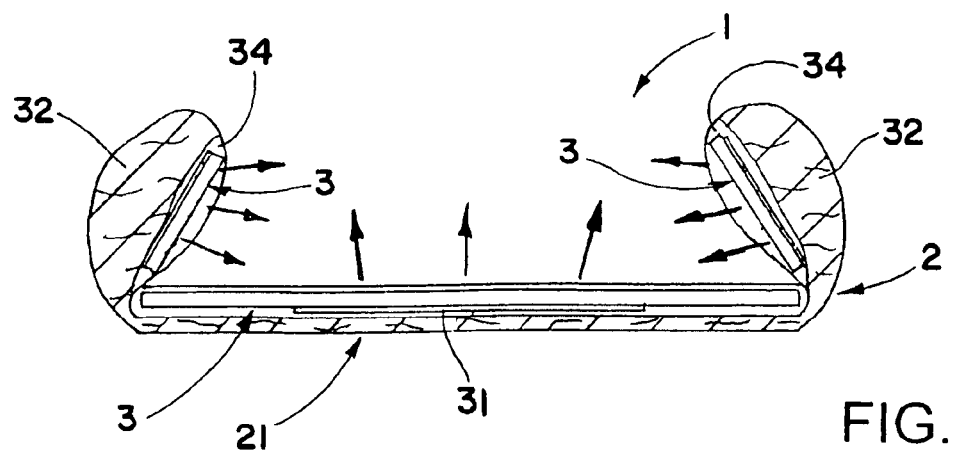
FIG. 5 is a schematic transverse section through another form of phototherapy positioning system of the present invention including multiple phototherapy light emitters attached to the pad bottom and one or more padded walls for directing light toward an infant when positioned on the pad.
Figure 6:
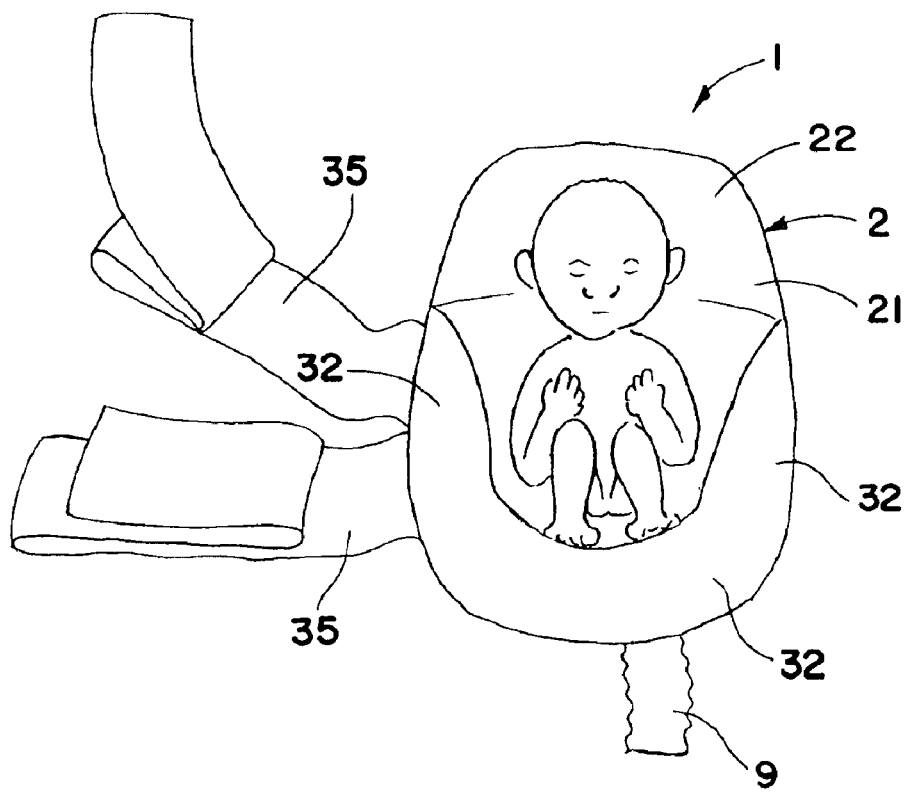
FIG. 6 is a schematic top plan view of the phototherapy positioning system of FIG. 1 showing an infant placed on the pad.
Figure 7:
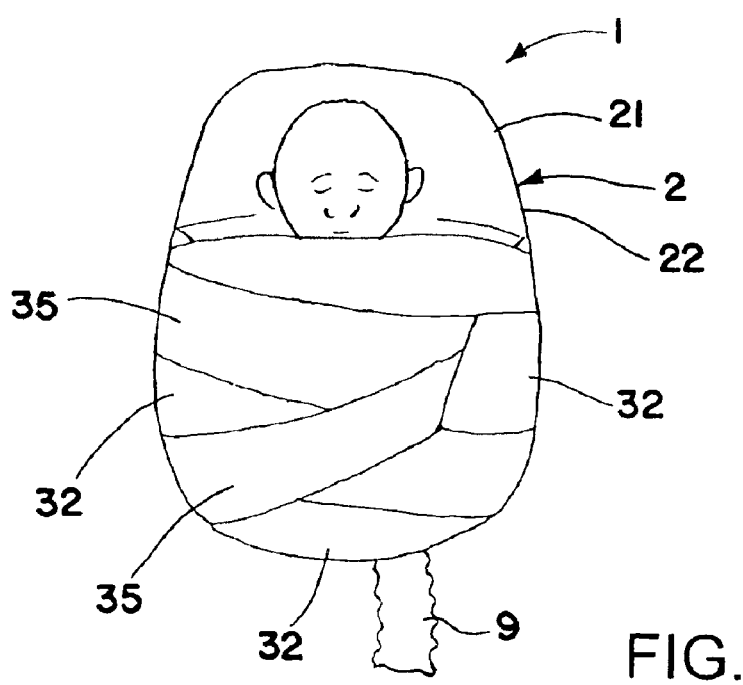
FIG. 7 is a schematic top plan view similar to FIG. 6 but showing the infant being restrained in a preferred position on the pad to minimize stress on the infant during phototherapy treatment.
Figure 8:
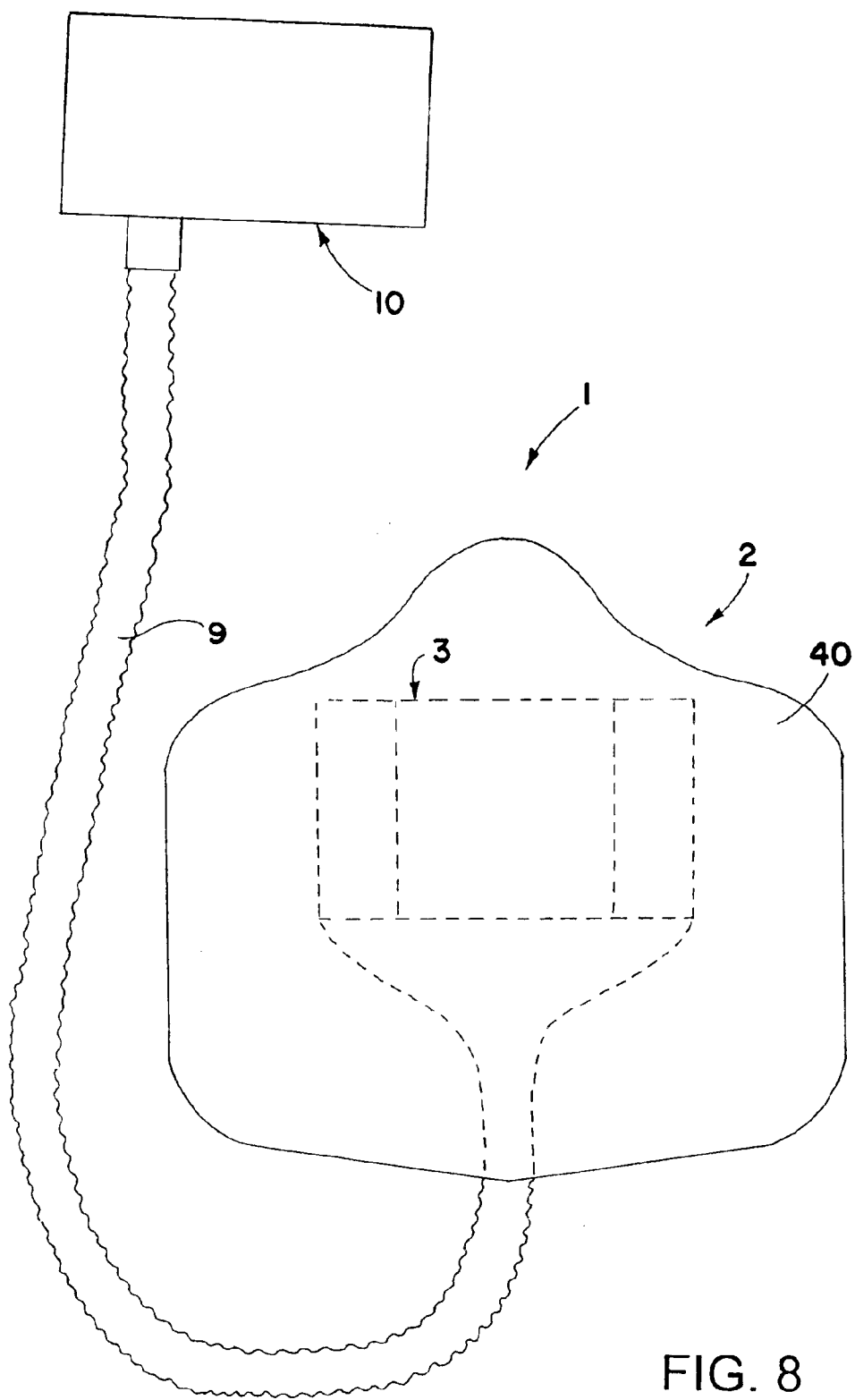
FIG. 8 is a schematic top plan view of another phototherapy positioning system of the present invention in the form of a blanket having a phototherapy light emitter attached thereto.

Pad 2 may also have padded walls 32 extending around one end for the infant to push its legs against and at least part way along opposite side edges to aid in positioning and restraining the infant including the infant's arms, shoulders, hips and legs on the pad bottom 21 as schematically shown in FIG. 6. Suitable attachment means or pockets 34 may also be provided in or on one or more of the padded side walls 32 for receiving one or more additional light emitters for directing additional light toward the infant as schematically shown in FIG. 5. Moreover, one or more securing means 35 such as ties, snaps, buckles and/or Velcro fasteners or the like may be used for maintaining the infant in a "fetal" type position on the pad as schematically shown in FIGS. 6 and 7 or as dictated by the care giver to minimize stress on the infant during phototherapy treatment.

Alternatively, the pad 2 may be more in the shape of a blanket 40 as schematically shown in FIGS. 8–11. Also the blanket 40 may be padded and/or quilted to give the blanket additional softness, and may be provided with a pocket 4 for receipt of a light emitter 3 as schematically shown in FIG. 9, or the light emitter may be attached to the blanket using any of the other attachment means 5 previously described.

FIG. 10 schematically shows an infant placed on the blanket 40 in overlying relation to the light emitter 3, whereas FIG. 11 shows the blanket 40 wrapped around the infant for positioning and restraining the infant, including the arms and shoulders as well as the hips and legs of the infant in a fetal type position or as dictated by the care giver to minimize stress on the infant during phototherapy treatment.

Although the invention has been shown and described with respect to certain embodiments, it is obvious that equivalent alterations and modifications will occur to others skilled in the art upon the reading and understanding of the specification. In particular, with regard to the various functions performed by the above described components, the term (including any reference to a "means") used to describe such components are intended to correspond, unless otherwise indicated, to any component which performs the specified function of the described component (e.g., that is functionally equivalent), even though not structurally equivalent to the disclosed component which performs the functions in the herein exemplary embodiments of the invention. In addition, while a particular feature of the invention may have been disclosed with respect to only one embodiment, such feature may be combined with one or more other features of other embodiments as may be desired or advantageous for any given or particular application.

What is claimed is:

1. A phototherapy positioning system for an infant comprising a flexible cloth-like pad having a pad bottom on which an infant is positioned during phototherapy treatment, and a phototherapy light emitter attachable to the pad for directing light toward the infant when positioned on the pad bottom, the pad bottom having a padded wall at one end extending above the pad bottom for the infant to push its legs against during phototherapy treatment.

2. The system of claim 1 wherein the light emitter is attached to the pad bottom.

3. The system of claim 1 wherein the light emitter comprises an optic light guide.

4. The system of claim 3 wherein the light guide comprises one or more layers of optical fibers.

5. The system at claim 4 wherein the light guide is flexible.

6. The light emitter of claim 3 wherein the light guide is a one-piece molded light guide.

7. The system of claim 6 wherein the light guide is flexible.

8. The system of claim 6 wherein the light guide is rigid.

9. The system of claim 3 further comprising a light distributor for receiving light from a remote light source and transmitting the light to the light emitter via internal reflection.

10. The system of claim 1 wherein the light emitter comprises an array of lights.

11. The system claim 10 wherein the lights are LEDs.

12. The system of claim 1 wherein attachment means comprising at least one of snaps, buckles, hook and loop fasteners, clips, adhesive strips, and ties are provided for attaching the light emitter to the pad.

13. The system of claim 1 wherein the light emitter is removable from the pad.

14. The system of claim 1 wherein the light emitter is integrated into the pad.

15. The system of claim 1 wherein the pad has padded side walls extending above the pad bottom along at least portions of the length of the pad to aid in positioning and restraining the infant on the pad.

16. The system of claim 15 wherein phototherapy light emitters are attached to the pad bottom and at least one side wall for directing light toward the infant during phototherapy treatment.

17. A phototherapy positioning system for an infant comprising a flexible cloth-like pad having a pad bottom on which an infant is positioned during phototherapy treatment, the pad including one or more padded walls extending above an end or side of the pad bottom, and a phototherapy light emitter attachable to one or more of the padded walls for directing light toward the infant when positioned on the pad bottom for exposing the infant to the light during phototherapy treatment.

18. The system of claim 17 wherein one or more of the padded walls includes a pocket for receipt of the light emitter.

19. A phototherapy positioning system for an infant comprising a flexible cloth-like pad for use in positioning an infant during phototherapy treatment, the pad including a pad bottom having at least two chambers, a phototherapy light emitter in one of the chambers for directing light toward an infant positioned on the pad, the other chamber containing a relatively soft fill material, at least portions of the pad overlying the light emitter being transparent or translucent to allow a portion of the light emitted by the light emitter to pass for exposing the infant to the light during phototherapy treatment.

20. The system of claim 19 wherein the light emitter is flexible, and the chamber for receiving the light emitter is above the chamber containing the fill material and has a transparent or translucent outer fabric layer that allows light from the light emitter to pass for exposing the infant to the light during phototherapy treatment.

21. The system of claim 19 wherein the chamber containing the fill material is above the chamber for receiving the light emitter, and at least portions of the fill material and fabric layers that form the chambers are made of a transparent or translucent material that allow light from the light emitter to pass for exposing the infant to the light during phototherapy treatment.

22. The system of claim 21 wherein the fill material is a transparent or translucent gel.

23. The system of claim 19 wherein the pad is in the form of a blanket that is foldable around the infant, and the light emitter has a width and length less than the width and length of the blanket.

24. The system of claim 19 wherein the pad is insulated to help the infant retain warmth.

25. The system of claim 19 wherein at least portions of the pad are quilted to give the pad additional softness.

26. The system of claim 19 further comprising means for positioning and restraining the infant including the infant's arms, shoulders, hips and legs on the pad during phototherapy treatment.

27. The system of claim 26 wherein the positioning and restraining means comprises at least one of ties, snaps, buckles and hook and loop fasteners.

28. A phototherapy positioning system for an infant comprising a flexible cloth-like pad for use in positioning an infant during phototherapy treatment, a phototherapy light emitter attached to the pad for directing light toward an infant positioned on the pad, at least portions of the pad overlying the light emitter being transparent or translucent to allow a portion of the light emitted by the light emitter to pass for exposing the infant to the light during phototherapy treatment, the light emitter comprising one or more layers of flexible optical fibers having sides that are foldable over a top surface of the optical fiber layers to permit the light emitter to be used with different width pads, the light emitter having a back reflector that terminates short of the foldable sides so the back reflector does not interfere with the light emitted by the light emitter along the sides when the sides are folded over.

29. A phototherapy positioning system for an infant comprising a flexible cloth-like pad having a pad bottom on which an infant is positioned during phototherapy treatment, a phototherapy light emitter, a pocket on or in the pad for receiving the phototherapy light emitter for directing light toward the infant when positioned on the pad bottom, at least portions of the pad overlying the light emitter being transparent or translucent to allows portion of the light emitted by the light emitter to pass for exposing the infant when positioned on the pad bottom to the light during phototherapy treatment, and padded end and side walls extending above the pad bottom along one end and along at least portions of the length of the pad to aid in positioning and restraining the infant during phototherapy treatment.

30. The system of claim 29 wherein the pocket is in the pad bottom, and one or more additional pockets are provided in one or more of the side walls of the pad for receipt of additional light emitters for directing light toward an infant when positioned on the pad bottom.

* * * * *